United States Patent
Papenfuss et al.

(10) Patent No.: US 8,366,559 B2
(45) Date of Patent: Feb. 5, 2013

(54) CANNULATED FLEXIBLE DRIVE SHAFT

(75) Inventors: Erik H. Papenfuss, Naples, FL (US); Hans B. Papenfuss, Naples, FL (US)

(73) Assignee: Lenkbar, LLC, Pensacola, FL (US)

( * ) Notice: Subject to any disclaimer, the term of this patent is extended or adjusted under 35 U.S.C. 154(b) by 107 days.

(21) Appl. No.: 12/968,556

(22) Filed: Dec. 15, 2010

(65) Prior Publication Data

US 2011/0319896 A1 Dec. 29, 2011

Related U.S. Application Data

(60) Provisional application No. 61/357,651, filed on Jun. 23, 2010.

(51) Int. Cl.
*F16D 3/18* (2006.01)
(52) U.S. Cl. .......................................... 464/149; 606/80
(58) Field of Classification Search .................. 464/78, 464/149; 606/80
See application file for complete search history.

(56) References Cited

U.S. PATENT DOCUMENTS

| 338,310 | A | | 3/1886 | Smith |
|---|---|---|---|---|
| 1,314,601 | A | * | 9/1919 | McCaskey ................ 464/149 X |
| 5,344,399 | A | | 9/1994 | DeVries |
| 5,464,407 | A | | 11/1995 | McGuire |
| 5,562,667 | A | | 10/1996 | Shuler et al. |
| 5,584,839 | A | | 12/1996 | Gieringer |
| 5,681,333 | A | | 10/1997 | Burkhart et al. |
| 5,722,425 | A | | 3/1998 | Bostrom |
| 5,797,918 | A | | 8/1998 | McGuire et al. |
| 6,010,507 | A | | 1/2000 | Rudloff |
| 6,053,922 | A | | 4/2000 | Krause et al. |
| 6,214,012 | B1 | | 4/2001 | Karpman et al. |
| 6,447,518 | B1 | | 9/2002 | Krause et al. |
| 6,689,132 | B2 | | 2/2004 | Biscup |
| 7,413,563 | B2 | | 8/2008 | Corcoran et al. |
| 7,579,550 | B2 | | 8/2009 | Dayton et al. |
| 7,604,643 | B2 | | 10/2009 | Ciccone et al. |
| 2005/0033365 | A1 | | 2/2005 | Courage |
| 2008/0221392 | A1 | | 9/2008 | Jorgensen |
| 2009/0099554 | A1 | | 4/2009 | Forster et al. |
| 2009/0182288 | A1 | | 7/2009 | Spenciner |

FOREIGN PATENT DOCUMENTS

| CN | 2642256 | | 9/2004 |
|---|---|---|---|
| EP | 2140824 | | 1/2010 |
| EP | 2140824 | | 6/2010 |
| GB | 19223 | * | 0/1897 |
| WO | WO 01/35839 | | 5/2001 |

OTHER PUBLICATIONS

"Endius launches NorthStar Cannulated Screw Delivery System," Biotech Week Oct. 2006.
"Strategic Orthopaedics," by Jackie Orsagh, Business People Sep. 2006.
"Percutaneous Closed Reduction of Fracture Dislocation of the Shoulder," by Silver et al., dated Jul. 2004.

\* cited by examiner

*Primary Examiner* — Gregory Binda
(74) *Attorney, Agent, or Firm* — RatnerPrestia

(57) ABSTRACT

A flexible cannulated drive shaft having a plurality of interlocking sections having multi-angled dovetails cut into the drive shaft. Each dovetail design is made up of substantially triangular-shaped pins and substantially triangular-shaped sockets that alternate around the circumference of each interlocking section. The pins of one interlocking section moveably engage the sockets of a second interlocking section and vice versa. Furthermore, the substantially triangular-shaped pins and substantially triangular-shaped sockets stay locked together whether the drive shaft is being rotated clockwise or counterclockwise. Angled surfaces add greater stability to the drive shaft and prevent the interlocking sections from coming apart.

23 Claims, 4 Drawing Sheets

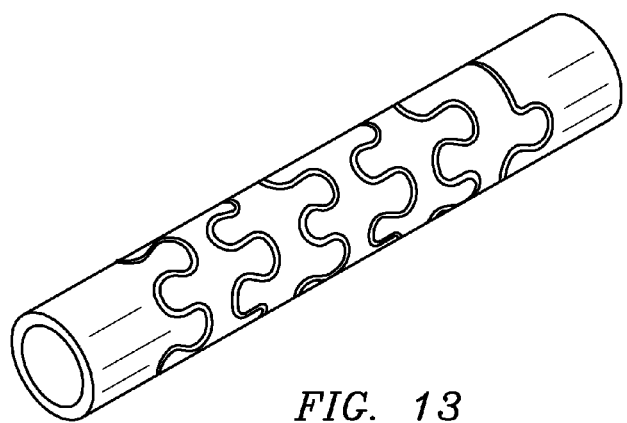
FIG. 13
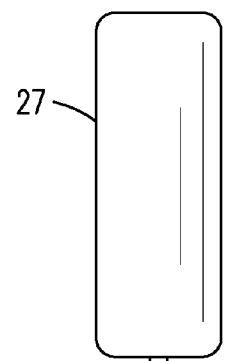
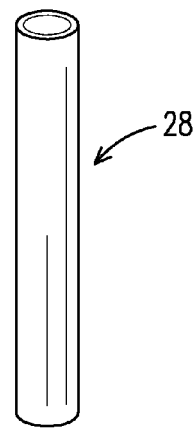
FIG. 14
FIG. 12

CANNULATED FLEXIBLE DRIVE SHAFT

CROSS REFERENCE TO RELATED APPLICATION

This application claims the benefit of U.S. Provisional Patent Application No. 61/357,651, filed Jun. 23, 2010. The patent application identified above is incorporated herein by reference in its entirety to provide continuity of disclosure.

BACKGROUND OF THE INVENTION

This invention relates to tools used for performing surgeries, such as arthroscopic or orthopedic procedures, more particularly, a cannulated flexible drive shaft having a plurality of interlocking sections, preferably locked together by multi-angled dovetails, along the shaft that allow a distal end to be flexible while withstanding the torque from being rotated clockwise or counterclockwise thereby preventing the dovetails from separating and failing.

The limitations on maneuverability imposed by arthroscopic surgery mean that conventional straight drive shafts are not well suited for such procedures. Therefore, various arthroscopic surgical procedures utilize flexible drive shafts to drill into bone, ream bone, punch holes into bone, push anchors or screws into bone, tap anchors or screws into bone, screw anchors or screws into bone and securing sutures to bone, tendons and so forth. Conventional flexible drive shafts have a helical coil located along the entire drive shaft or along a portion of the distal end of the drive shaft. The helical coil allows a user to pass the drive shaft through a bent guide. However, depending on the orientation of a helical design, the coils will tighten together when turned clockwise and separate or pull apart when turned counterclockwise or vice versa for drive shafts having a helical design with an opposite orientation. Therefore, currently a surgeon needs two flexible drive shafts. One that will transmit torque in a clockwise direction and one that will transmit torque in a counter-clockwise direction.

Therefore, a need exists for a cannulated flexible drive shaft that will transmit torque in a clockwise direction as well as a counterclockwise direction without the drive shaft being pulled apart.

| Patent/Serial No. | Inventor | Issue/Publication Date |
|---|---|---|
| U.S. patent Documents | | |
| 7,604,643 | Ciccone et al. | Oct. 20, 2009 |
| 2009/0182288 | Spenciner | Jul. 16, 2009 |
| 2008/0221392 | Jorgensen | Sep. 11, 2008 |
| 2005/0033365 | Courage | Feb. 10, 2005 |
| 6,447,518 | Krause et al. | Sep. 10, 2002 |
| 6,214,012 | Karpman et al. | Apr. 10, 2001 |
| 6,053,922 | Krause et al. | Apr. 25, 2000 |
| 6,010,507 | Rudloff | Jan. 04, 2000 |
| 5,681,333 | Burkhart et al. | Oct. 28, 1997 |
| 5,584,839 | Gieringer | Dec. 17, 1996 |
| 5,562,667 | Shuler et al. | Oct. 08, 1996 |
| 5,464,407 | McGuire | Nov. 07, 1995 |
| Foreign Patent Documents | | |
| EP2140824 | Biederman et al. | Jun. 01, 2010 |
| CN2642256 | Wang | Sep. 22, 2004 |
| Other Publications | | |

"Percutaneous Closed Reduction of Fracture Dislocation of the Shoulder," by Silver et al.; July 2004; "Endius launches NorthStar Cannulated Screw Delivery System," Biotech Week October, 2006; "Strategic Orthopaedics," by Jackie Orsagh, Business People September, 2006.

SUMMARY OF THE INVENTION

The primary object of the present invention is to provide a flexible drive shaft that will transmit torque in a clockwise direction as well as a counterclockwise direction.

A further object of the present invention is to provide a flexible drive shaft that is strong enough to withstand the torque being placed on it while in use.

The present invention fulfills the above and other objects by providing a flexible cannulated drive shaft having a plurality of interlocking sections having an angled dovetail design cut into the drive shaft. Each interlocking section has a proximal end, a distal end and a dovetail design comprising substantially triangular-shaped pins and substantially triangular-shaped sockets that alternate around the circumference of the proximal end and/or distal end of each interlocking section. The pins of one interlocking section moveably engage the sockets of a second interlocking section and vice versa. The substantially triangular-shaped pins and substantially triangular-shaped sockets secure the interlocking sections together while allowing the drive shaft to be flexible. An additional benefit of the interlocking sections is that the distance between each section may be cut larger or smaller to achieve a more or less flexible drive shaft. Furthermore, the substantially triangular-shaped pins and substantially triangular-shaped sockets stay locked together whether the drive shaft is being rotated clockwise or counterclockwise. The drive shaft may be used as a manual tool, such as a screw driver, or attached to a rotational tool, such as a drill. A guide allows a user to control the placement and depth of the distal end of the drive shaft during operations.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 12 is a side view of an internal guide of the present invention;

FIG. 13 is a side perspective view of a flexible cannulated drive shaft of the present invention comprising a dovetail design having substantially round-shaped pins and substantially round-shaped sockets; and FIG. 14 is a protective sheath of the present invention.

DESCRIPTION OF THE PREFERRED EMBODIMENTS

Figure 1:
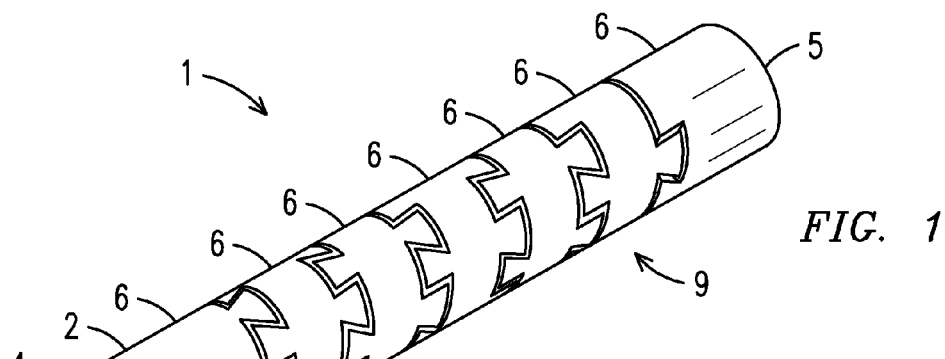
FIG. 1 is an isometric perspective view of a flexible cannulated drive shaft of the present invention.
Figure 2:
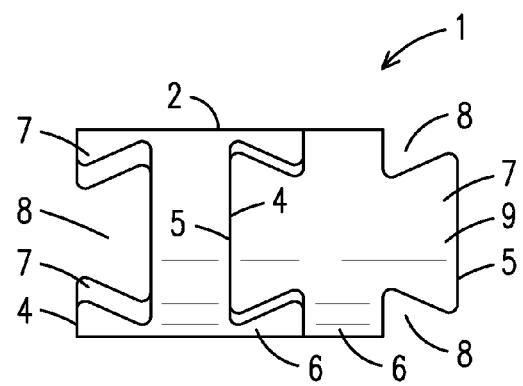
FIG. 2 is a side view of dovetail sections from a flexible cannulated drive shaft of the present invention.

For purposes of describing the preferred embodiment, the terminology used in reference to the numbered components in the drawings is as follows:

1. drive shaft
2. outer surface
3. inner surface
4. proximal end
5. distal end
6. interlocking section
7. pin
8. socket
9. template
10. tubular shaft
11. cut
12. edge
13. screw driver
14. suture anchor
15. handle
16. hollow portion
17. external guide
18. stop
19. head
20. suture
21. inward angled surface
22. outward angled surface
23. inner portion of socket
24. side portion of pin
25. outer portion of pin
26. internal guide
27. handle
28. protective sheath With reference to FIGS. 1 and 2, a side perspective view of a flexible cannulated drive shaft 1 of the present invention and a side view of interlocking sections 6 of the present invention, respectively, are shown. The drive shaft 1 is preferably tubular and comprises an outer surface 2, an inner surface 3, a proximal end 4 and a distal end 5. A plurality of interlocking sections 6 are located along the drive shaft 1. As shown in FIG. 2, each interlocking section 6 has a proximal end 4, a distal end 5 and a dovetail design 9 comprising substantially triangular-shaped pins 7 and substantially triangular-shaped sockets 8 that alternate around the circumference of the proximal end 4 and/or distal end 5 of each interlocking section 6. The preferred shape of the pins 7 and sockets 8 is substantially triangular shaped, however the pins 7 and sockets 8 may also be substantially round shaped.

The pins 7 of one interlocking section 6 moveably engage the sockets 8 of a second interlocking section 8 and vice versa. The substantially triangular-shaped pins 7 and substantially triangular-shaped sockets 8 secure the interlocking sections 6 together while allowing the drive shaft 1 to be flexible. The substantially triangular-shaped pins 7 and corresponding substantially triangular-shaped sockets 8 are cut at opposing angles (as illustrated further in FIGS. 4-10) to allow for increased flexibility and to further lock the sections 6 together and prevent the interlocking sections from separating. Furthermore, the substantially triangular-shaped pins 7 and substantially triangular-shaped sockets 8 stay locked together whether the drive shaft 1 is being rotated clockwise or counterclockwise.

Figure 3:
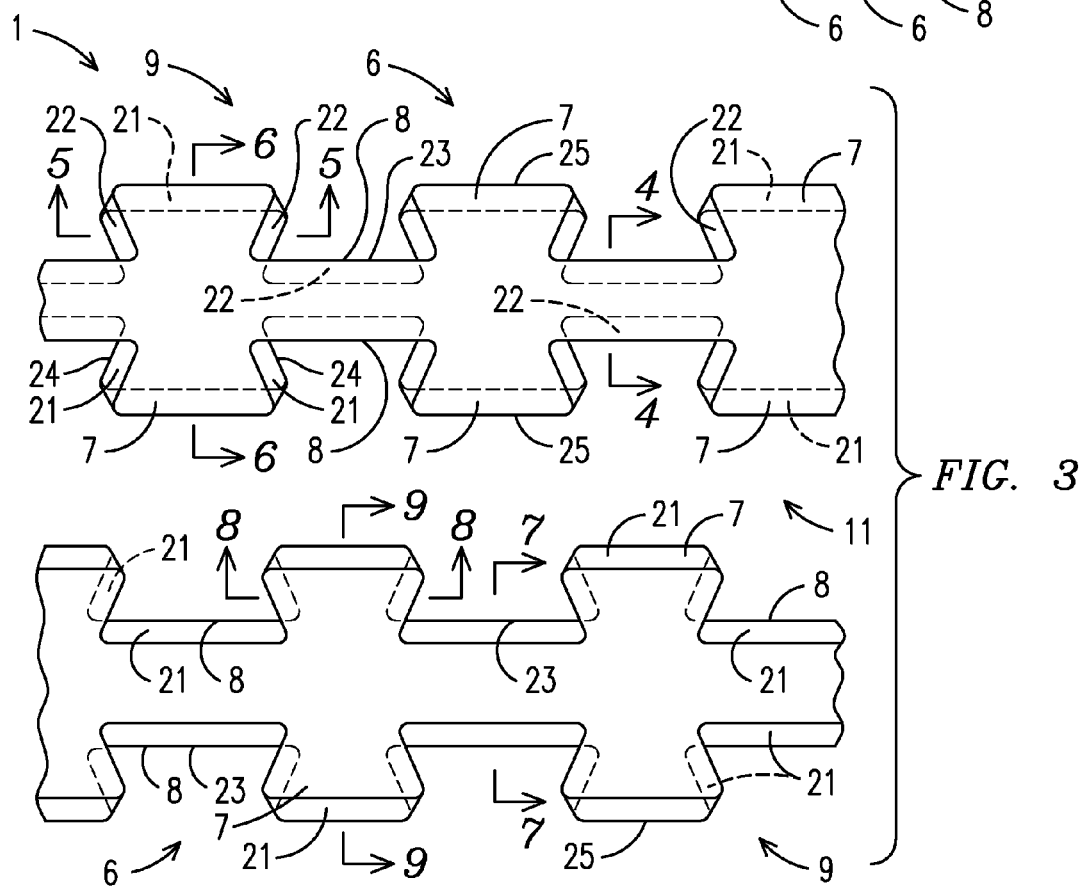
FIG. 3 is an exploded top plan view of a laid flat interlocking section dovetail design and a top view of a laid flat opposing interlocking section dovetail design of the present invention.

Now referring to FIG. 3, an exploded top view of a laid flat interlocking section 6 dovetail design 9 and a top view of a laid flat opposing interlocking section 6 dovetail design 9 of the present invention is shown. The flexible portion of the drive shaft 1 is made by cutting interlocking sections 6 into a tubular shaft 10. Each cut 11 is made around the entire circumference of the tubular shaft 10 to create a dovetail design 9 comprising alternating substantially triangular-shaped pins 7 and substantially triangular-shaped sockets 8. The substantially triangular-shaped pins 7 and corresponding substantially triangular-shaped sockets 8 are cut at opposing angles to allow for increased flexibility and to further lock the sections 6 together and prevent the interlocking sections from separating. Each triangular-shaped pin 7 has inward angled surfaces 21 and outward angled surfaces 22 that correspond to inward angled surfaces 21 and outward angled surfaces 22 of an opposing triangular-shaped socket 8. The inward angled surfaces 21 or outward angled surfaces 22 may be located on inner portions 23 of triangular-shaped sockets 8, side portions 24 of triangular-shaped pins 7 or outer portions 25 of triangular-shaped pins 7.

Figure 4:
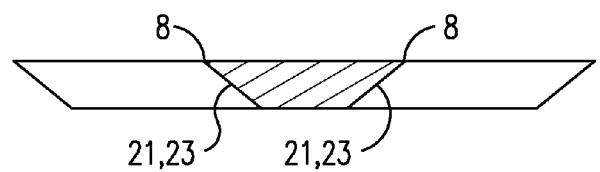
FIG. 4 a cross section of an interlocking section along line 4-4 of FIG. 3.

Now referring to FIG. 4, a cross section of an interlocking section along line 4-4 of FIG. 3 showing inward angled surfaces 21 located on inner portions 23 of triangular-shaped sockets 8.

Figure 5:
FIG. 5 a cross section of an interlocking section along line 5-5 of FIG. 3.

Now referring to FIG. 5, a cross section of an interlocking section along line 5-5 of FIG. 3 showing outward angled surfaces 22 located on side portions 24 of a triangular-shaped pin 7.

Figure 6:
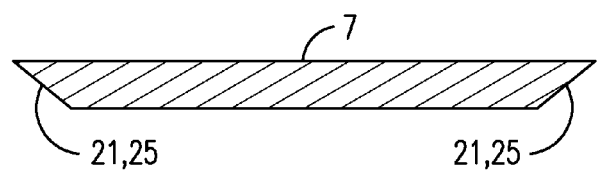
FIG. 6 a cross section of an interlocking section along line 6-6 of FIG. 3.

Now referring to FIG. 6, a cross section of an interlocking section along line 6-6 of FIG. 3 showing inward angled surfaces 21 located on outer portions 25 of triangular-shaped pins 7.

Figure 7:
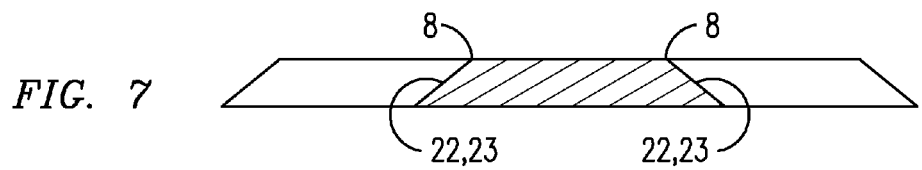
FIG. 7 a cross section of an interlocking section along line 7-7 of FIG. 3.

Now referring to FIG. 7, a cross section of an interlocking section along line 7-7 of FIG. 3 showing outward angled surfaces 22 located on inner portions 23 of triangular-shaped sockets 8.

Figure 8:
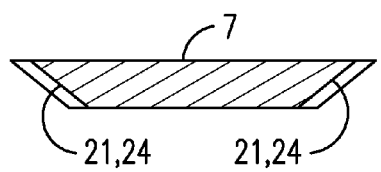
FIG. 8 a cross section of an interlocking section along line 8-8 of FIG. 3.

Now referring to FIG. 8, a cross section of an interlocking section along line 8-8 of FIG. 3 showing inward angled surfaces 21 located on side portions 24 of a triangular-shaped pin 7.

Figure 9:
FIG. 9 a cross section of an interlocking section along line 9-9 of FIG. 3.

Now referring to FIG. 9, a cross section of an interlocking section along line 9-9 of FIG. 3 showing outward angled surfaces 22 located on outer portions 25 of triangular-shaped pins 7.

Figures 10, 11:
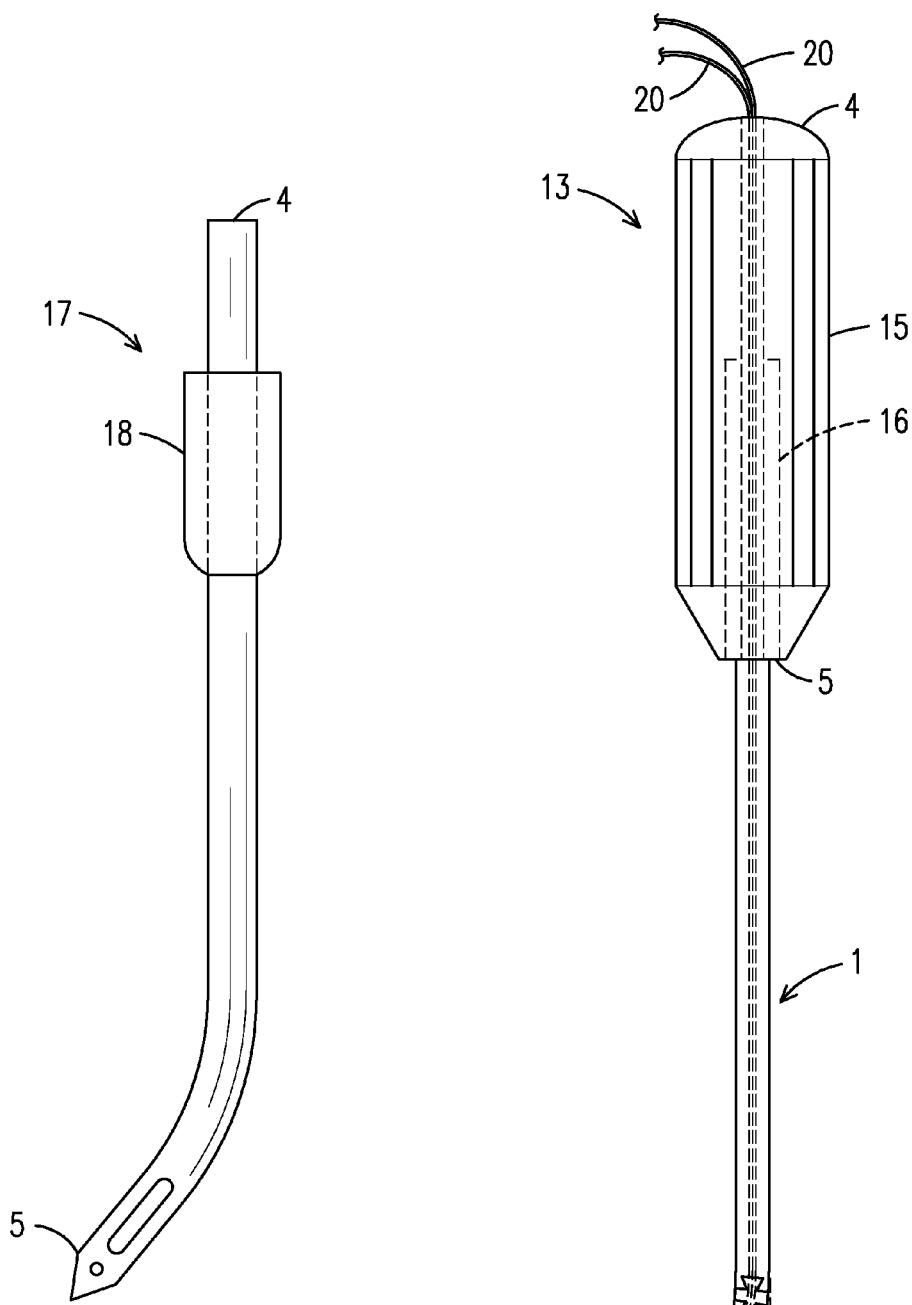
FIG. 10 is a side plan view of a screwdriver having a flexible cannulated drive shaft of the present invention therein.
FIG. 11 is a side plan view of an external guide of the present invention.

Now referring to FIG. 10, a side plan view of a screwdriver 13 having a flexible cannulated drive shaft 1 of the present invention therein is shown. The screwdriver 13 may be used for inserting a suture anchor 14 into a bone. The screwdriver 13 comprises a proximal end 4 and a distal end 5. A handle 15 is located on the proximal end 4 of the screw driver 13. A flexible cannulated drive shaft 1 extends outward from the distal end 5 of the handle 15. A hollow portion 16 of the handle 15 accepts a proximal end 4 of an external guide 17 (as shown in FIG. 11) and works in conjunction with a stop 18 located on the guide 17 to control the distance that the drive shaft 1 is able to extend from a distal end 5 of the guide 17. A head 19 located on the distal end 5 of the drive shaft 1 is used to engage and rotate the suture anchor 14. A plurality of interlocking sections 6 are located along the drive shaft 1 near the distal end 5 of the screwdriver 13. The handle 15 of the screwdriver 13 is preferably tubular to allow for a suture 20 attached to the suture anchor 14 to be passed through the handle 15. Although the flexible cannulated drive shaft 1 shown here is attached to a handle 15, it may be attached to any rotational tool, such as a drill.

Now referring to FIG. 11, a side plan view of an external guide 17 of the present invention is shown. The external guide 17 is preferably a tubular shaft having a proximal end 4 and a distal end 5. The external guide 17 may be bent and curved to control the positioning of the drive shaft 1 during operations. The distal end 8 of the external guide 17 is preferably pointed so that the pointed distal end can be inserted into a bone, thereby locking the external guide 17 in place on the bone. A stop 18 is located on the near the proximal end 4 of the external guide 17. A hollow portion 16 of the handle 15 (as shown in FIG. 10) accepts the proximal end 4 of the external guide 17 and works in conjunction with the stop 18 located on the external guide 17 to control the depth that the drive shaft 1 is able to extend out of the distal end 5 of the external guide 17. The stop 18 may be adjustable to allow a user to increase the distance between the proximal end 4 of the external guide 17 and the stop 18.

Now referring to FIG. 12, a side view of an internal guide 26 of the present invention is shown. The internal guide 26 is preferably a tubular shaft having a proximal end 4 and a distal end 5. A handle 27 is preferably located on the proximal end 4 of the internal guide 26. The internal guide 26 is preferably constructed from shape memory alloy or any other shape memory material that has an elastic effect, thereby allowing a user to forge a constant curve in the material that can be temporarily straitened when pressure is applied the curve. The internal guide 26 is used to control the positioning of the drive shaft 1 during operations. The curved section of the internal guide 26 may be temporarily straitened to be passed through the tubular handle 15 of the screwdriver 13 and through the cannulated drive shaft 1. The curved section of the internal guide 26 will the return to its curved shape, thereby placing a desired curve in the flexible portion of the cannulated drive shaft 1.

Now referring to FIG. 13, a side perspective view of a flexible cannulated drive shaft 1 of the present invention comprising a dovetail design 9 having substantially round-shaped pins 7 and substantially round-shaped sockets 8

Finally referring to FIG. 14, a protective sheath 28 of the present invention is shown. The protective sheath 28 is preferable made of a plastic or rubber material and is placed over the cannulated drive shaft 1 to cover the interlocking sections 6. The protective sheath 28 prevents the gaps between the interlocking sections 6 from becoming filled with foreign matter.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, we claim:

1. A cannulated flexible drive shaft comprising:
    a tubular shaft having a proximal end, a distal end, an inner surface and an outer surface; and
    at least two interlocking sections located on the tubular shaft, said at least two interlocking sections each having at least one pin and at least one socket,
    said at least two interlocking sections comprising a first interlocking section and a second interlocking section,
    the at least one pin on the first interlocking section having a circumferential width that increases as said at least one pin on the first interlocking section extends from the outer surface of the shaft to the inner surface of the shaft, so that said at least one pin on the first interlocking section becomes gradually wider toward the inner surface,
    the at least one pin on the second interlocking section having a circumferential width that decreases as said at least one pin on the second interlocking section extends from the outer surface of the shaft to the inner surface of the shaft, so that said at least one pin on the second interlocking section becomes gradually narrower toward the inner surface.

2. The cannulated flexible drive shaft of claim 1 wherein: said at least two interlocking sections are cut at opposing angles to create at least one inward angled surface and at least one outward angled surface; and said at least one inward angled surface is adjacent to the at least one outward angled surface.

3. The cannulated flexible drive shaft of claim 1 wherein: each of the pins is substantially triangular shaped; and each of the sockets is substantially triangular shaped.

4. The cannulated flexible drive shaft of claim 3 wherein: the pins and sockets are cut at opposing angles to create at least one inward angled surface and at least one outward angled surface; and said at least one inward angled surface is adjacent to the at least one outward angled surface.

5. The cannulated flexible drive shaft of claim 1 wherein: each of the pins is substantially round shaped; and each of the sockets is substantially round shaped.

6. The cannulated flexible drive shaft of claim 5 wherein: the pins and sockets are cut at opposing angles to create at least one inward angled surface and at least one outward angled surface; and said at least one inward angled surface is adjacent to the at least one outward angled surface.

7. The cannulated flexible drive shaft of claim 1 further comprising: a handle located on the proximal end of the tubular shaft.

8. The cannulated flexible drive shaft of claim 7 wherein: said handle is substantially tubular, thereby allowing a user to pass an object through the handle and through the tubular shaft.

9. The cannulated flexible drive shaft of claim 1 further comprising: a substantially tubular shaped external guide configured for placement over the external surface of the drive shaft to control a curve of the tubular shaft.

10. The cannulated flexible drive shaft of claim 1 further comprising: an internal guide configured for placement into the tubular shaft to control a curve of the tubular shaft.

11. The cannulated flexible drive shaft of claim 10 wherein: said internal guide is constructed out of a shape memory alloy.

12. The cannulated flexible drive shaft of claim 1 further comprising: a protective sheath configured to cover a predetermined portion of the external surface of the tubular shaft.

13. A cannulated flexible drive shaft comprising:
    a tubular shaft having a proximal end, a distal end, an inner surface and an outer surface; and
    at least two interlocking sections located on the tubular shaft, said at least two interlocking sections each having at least one pin and at least one socket,
    said at least two interlocking sections are cut at opposing angles to create at least one inward angled surface and at least one outward angled surface, said at least one inward angled surface is adjacent to the at least one outward angled surface,
    said at least two interlocking sections comprising a first interlocking section and a second interlocking section,
    the at least one pin on the first interlocking section having a circumferential width that increases as said at least one pin on the first interlocking section extends from the outer surface of the shaft toward the inner surface of the shaft, so that said at least one pin on the first interlocking section becomes gradually wider toward the inner surface, the at least one pin on the second interlocking section having a circumferential width that decreases as said at least one pin on the second interlocking section extends from the outer surface of the shaft toward the inner surface of the shaft, so that said at least one pin on the second interlocking section becomes gradually narrower toward the inner surface.

14. The cannulated flexible drive shaft of claim 13 wherein: each of the pins is substantially triangular shaped; and each of the sockets is substantially triangular shaped.

15. The cannulated flexible drive shaft of claim 14 wherein: the pins and sockets are cut at opposing angles to create said at least one inward angled surface and said at least one outward angled surface.

16. The cannulated flexible drive shaft of claim 13 wherein: each of the pins is substantially round shaped; and each of the sockets is substantially round shaped.

17. The cannulated flexible drive shaft of claim 16 wherein: the pins and sockets are cut at opposing angles to create said at least one inward angled surface and said at least one outward angled surface.

18. The cannulated flexible drive shaft of claim 13 further comprising: a handle located on the proximal end of the tubular shaft.

19. The cannulated flexible drive shaft of claim 18 wherein: said handle is substantially tubular, thereby allowing a user to pass an object through the handle and through the tubular shaft.

20. The cannulated flexible drive shaft of claim 13 further comprising: a substantially tubular shaped external guide configured for placement over the external surface of the drive shaft to control a curve of the tubular shaft.

21. The cannulated flexible drive shaft of claim 13 further comprising: an internal guide configured for placement into the tubular shaft to control a curve of the tubular shaft.

22. The cannulated flexible drive shaft of claim 21 wherein: said internal guide is constructed out of a shape memory alloy.

23. The cannulated flexible drive shaft of claim 13 further comprising: a protective sheath configured to cover a predetermined portion of the external surface of the tubular shaft.

* * * * *

UNITED STATES PATENT AND TRADEMARK OFFICE
CERTIFICATE OF CORRECTION

| | |
|---|---|
| PATENT NO. | : 8,366,559 B2 |
| APPLICATION NO. | : 12/968556 |
| DATED | : February 5, 2013 |
| INVENTOR(S) | : Papenfuss et al. |

It is certified that error appears in the above-identified patent and that said Letters Patent is hereby corrected as shown below:

In the Specifications:

Column 2, lines 51, 53, 55, 57, 59 and 61, the text "a cross section" should be changed to --is a cross section--.

Column 4, lines 26, 30, 34, 38, 42 and 46, the word "showing" should be changed to --shows--.

Column 5, line 11, the text "located on the near" should be changed to --located near--.

Column 5, line 28, the word "straitened" should be changed to --straightened--, and the text "applied the curve" should be changed to --applied to the curve--.

Column 5, line 31, the word "straitened" should be changed to --straightened--.

Column 5, lines 42-43, the work "preferable" should be changed to --preferably--.

Signed and Sealed this
Seventh Day of May, 2013

Teresa Stanek Rea
*Acting Director of the United States Patent and Trademark Office*